United States Patent [19]
Stroebel et al.

[11] Patent Number: 5,480,414
[45] Date of Patent: Jan. 2, 1996

[54] METHOD AND APPARATUS FOR CONTROLLING PACEMAKER DURING AUTOMATIC CAPTURE DETECTION

[75] Inventors: John C. Stroebel, Blaine; H. Toby Markowitz, Roseville, both of Minn.

[73] Assignee: Medtronic, Inc., Minneapolis, Minn.

[21] Appl. No.: 259,048

[22] Filed: Jun. 13, 1994

[51] Int. Cl.[6] ........................................... A61N 1/37
[52] U.S. Cl. ........................................................ 607/28
[58] Field of Search ............................................. 607/28

[56] References Cited

U.S. PATENT DOCUMENTS

| | | | |
|---|---|---|---|
| 3,920,024 | 11/1975 | Bowers | 607/28 |
| 3,949,758 | 4/1976 | Jirak | 607/28 |
| 4,428,378 | 1/1984 | Anderson | 607/28 |
| 4,485,813 | 12/1984 | Anderson | 607/28 |
| 4,556,063 | 12/1985 | Thompson | 607/28 |
| 4,708,142 | 11/1987 | Decote | 607/28 |
| 4,729,376 | 3/1988 | Decote | 607/28 |
| 5,127,404 | 7/1992 | Wyborny | 607/28 |
| 5,154,170 | 10/1992 | Bennett | 607/28 |

*Primary Examiner*—William E. Kamm
*Attorney, Agent, or Firm*—Michael B. Atlass; Harold R. Patton

[57] ABSTRACT

A cardiac pacemaker improves battery longevity by automatically providing optimized threshold amplitude and pulse width values. During capture verification and threshold searching, the pacemaker delivers a pacing pulse and a rapid, maximum amplitude backup pulse in case the pacing pulse fails to capture a patient's heart. Unlike the prior art, the backup pulse is delivered before a predefined Vulnerable Period (during which time pacing might lead to re-entrant tachycardia or fibrillation). This results in threshold searching which is quick, accurate and with smaller rate drops during loss of capture. In another aspect of the present invention, a diagnostic strength-duration curve is approximated by first setting the pulse width to a maximum value and determining the amplitude threshold (rheobase), and then by doubling the amplitude and determining the pulse width threshold (chronaxie).

5 Claims, 2 Drawing Sheets

METHOD AND APPARATUS FOR CONTROLLING PACEMAKER DURING AUTOMATIC CAPTURE DETECTION

FIELD OF THE INVENTION

The present invention generally relates to "capture" of the heart, here defined as the presence of contractions in the heart in direct response to electrical stimulation signals emanating from an artificial pacemaker ("pacemaker"). Also, the present invention relates to adjusting stimulation signal thresholds for pacemaker energy efficiency.

BACKGROUND OF THE INVENTION

Generally speaking, a cardiac pacemaker is an electrical device used to supplant some or all of an abnormal heart's natural pacing function, by delivering appropriately timed electrical stimulation signals designed to cause the myocardium of the heart to contract or "beat". Stimulation signals usually have well-defined amplitude and pulse width characteristics which can be adjusted to meet physiologic and device power conservation needs.

The strength (amplitude) and duration (pulse width) of the stimulation signals must be of such magnitude that capture is maintained, to prevent serious complications and even death. Yet, it is desirable for these magnitudes not to be higher than is needed for a reasonable safety margin for longer battery life. Chief among the problems is that stimulation signal thresholds necessary for maintaining capture often fluctuate in the short term, and gradually change in the long term. It has been clinically observed that the lowest threshold is observed immediately after implantation of the pacemaker (the acute threshold). Inflammation in the tissue around the tip of the stimulation electrode requires greater energy to propagate the stimulation signals, thereby driving the threshold up sharply during the first two to six weeks to its highest level (the peak threshold). Some of the inflammation reduces over the long-term, to lower the threshold below the peak level-the chronic threshold. However, the chronic threshold does not reduce to the acute level, since some permanent fibrous tissue, requiring greater energy than non-fibrous tissue for signal propagation, remains around the electrode tip. In the short-term, thresholds may decrease with exercise, for example, and may increase with various activities, including sleep.

Some prior art implantable pulse generators (IPGs) which serve as cardiac pacemakers have an automatic capture feature to maintain capture or restore capture after a loss-of-capture episode, without the need for clinical or patient intervention. In addition, some of these IPGs have an automatic threshold-seeking feature, which, either after capture restoration or periodically, seek the lowest "safe" voltage level of the stimulation signal for energy efficiency. That is, the voltage of the stimulation signal is lowered to the newly detected threshold voltage plus a safety margin, rather than using an unnecessarily high stimulation signal voltage level.

During the search for thresholds, some prior pacemakers deliver a backup pulse (as a safety measure) after a primary pacing pulse in case the primary pacing pulse fails to capture the patient's heart. The backup pulse is delivered after the passage of a predefined Vulnerable Period, as is well known in the art, to avoid facilitating re-entrant tachycardia and fibrillation. As a result, the aforementioned prior art pacemakers result in a drop in pacing rate and long threshold searching times. The patient may be aware of either the drop in pacing rate, or alternatively an artificially elevated rate used to compensate for the rate drop.

SUMMARY OF THE INVENTION

In view of the foregoing, the first object of the present invention is to provide a cardiac pacemaker having an automatic capture feature in which capture is maintained during automatic threshold-seeking.

The second object of the present invention is to provide a cardiac pacemaker having an automatic capture feature in which the pacing rate remains above bradycardic levels during threshold searches.

The third object of the present invention is to provide a cardiac pacemaker having an automatic capture feature in which data collected during operation of the feature is used for diagnostic purposes.

The fourth object of the present invention is to provide a cardiac pacemaker having an automatic capture feature which leads to increased battery life.

The fifth object of the present invention is to provide a cardiac pacemaker having an automatic capture feature which prevents patient discomfort during its operation.

The sixth object of the present invention is to provide a cardiac pacemaker having an automatic capture feature which has simple patient follow-up with feedback during automatic determination of pacing thresholds.

The seventh object of the present invention is to provide a cardia pacemaker with the ability to automatically generate a strength-duration curve base on amplitude and pulse width searches.

In order to satisfy the above object and others, the present invention provides a pacemaker capable of automatically seeking stimulation thresholds at least including:

a controller for controlling the operation of the pacemaker;

a pulse generator coupled to the controller for generating stimulation pulses;

a capture detector coupled to the controller for detecting the capture of a patient's heart in response to a stimulation pulse; and a threshold determining means coupled to the controller, to the pulse generator, and to the capture detector, for determining amplitude and pulse width thresholds of primary pacing pulses;

wherein the pulse generator at least includes:

primary pacing pulse generator for generating the primary pacing pulses; and backup pacing pulse generator for generating backup pacing pulses after the primary pacing pulses, but before the start of a predefined Vulnerable Period, defined as a period during which the delivery of cardiac stimulation pulses increases a patient's risk of arrythmia, wherein said backup pacing pulses have sufficiently large characteristics known to effect capture.

The present invention also provides in a pacemaker, an automatic stimulation threshold seeking method for automatically seeking stimulation signal thresholds, the method at least including the steps of:

generating stimulation pulses;

detecting the capture of a patient's heart in response to a stimulation pulse; and determining amplitude and pulse width thresholds of primary pacing pulses;

wherein the generating step at least includes the steps of:
  generating the primary pacing pulses; and
  generating backup pacing pulses after the primary pacing pulses, but before the start of a predefined Vulnerable Period, defined as a period during which the delivery of cardiac stimulation pulses increases a patient's risk of arrythmia, wherein said backup pacing pulses have sufficiently large characteristics known to effect capture.

The details of the present invention will be revealed in the following description, with reference to the attached drawing.

BRIEF DESCRIPTION OF THE DRAWING

The various figures of the drawing are briefly described as follows.

DETAILED DESCRIPTION OF THE INVENTION

PART I. DESCRIPTION OF PACEMAKER DEVICE

Figure 1:
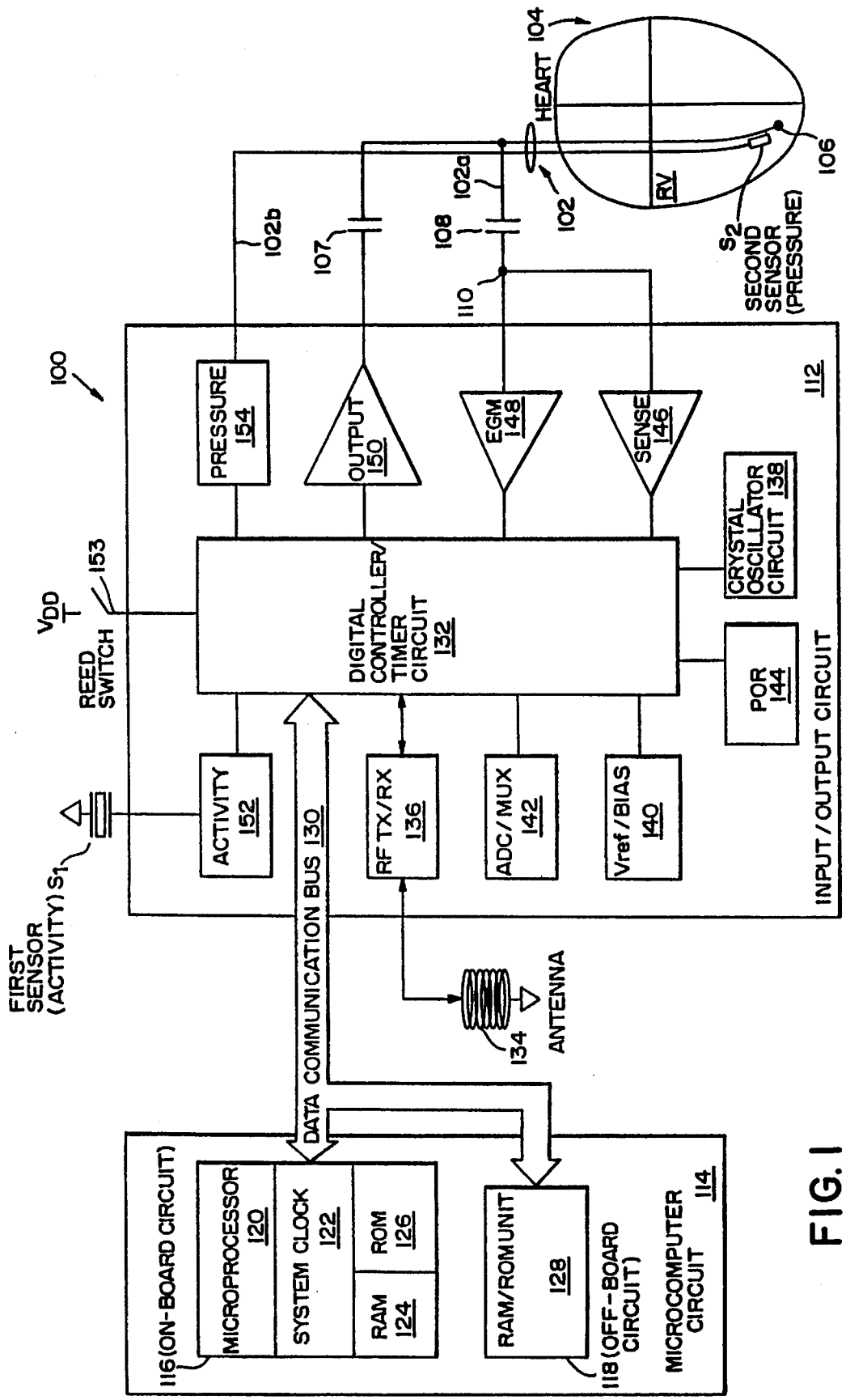
FIG. 1 is a schematic block diagram of a multi-sensor, rate-responsive, single chamber IPG capable of subsuming the present invention.

FIG. 1 is a block circuit diagram illustrating a multi-programmable, implantable, single-chamber, bradycardia pacemaker 100 capable of carrying out the present invention. This figure and related figures not presented in this letters patent are described in U.S. Pat. No. 5,154,170, issued Oct. 13, 1992, and titled OPTIMIZATION FOR RATE RESPONSIVE CARDIAC PACEMAKER, which patent is hereby incorporated by reference. Although the present invention is described in conjunction with a microprocessor-based architecture, it will be understood that it could be implemented in digital logic-based, custom integrated circuit (IC) architecture, if desired. It will also be understood that the present invention may be implemented in dual-chamber pacemakers, cardioverters, defibrillators and the like.

In the preferred embodiment of FIG. 1, pacemaker 100 includes two sensors, namely, $S_1$ and $S_2$, each of which provide a sensor output which varies as a function of a measured parameter that relates to the metabolic requirements of the patient. Since each sensor output can be utilized by pacemaker 100 to control its pacing rate, each sensor output is herein referred to as a rate-control parameter (RCP). Examples of an RCP include, for example, physical activity of the body, right ventricular blood pressure and the change of right ventricular blood pressure over time, venous blood temperature, venous blood oxygen saturation, respiration rate, minute ventilation, and various pre- and post-systolic time intervals measured by impedance or pressure sensing within the right ventricle of the heart.

In the preferred embodiment, first sensor $S_1$ comprises an activity sensor, such as a piezoelectric sensor of the type disclosed in U.S. Pat. No. 4,428,378 issued to Anderson et al., entitled "Rate Adaptive Pacer", which is held by the same assignee as the present invention and which is incorporated herein by reference. First sensor $S_1$ thus measures a rate-control parameter related to physiologic forces associated with body activity ($RCP_{act}$), and provides a first sensor output ($Output_{act}$) which is proportional to the patient's activity. Also in the preferred embodiment, second sensor $S_2$ comprises a dynamic pressure sensor, such as the type disclosed in U.S. Pat. No. 4,485,813 issued to Anderson et al., entitled "Implantable Dynamic Pressure Transducer System", which is held by the same assignee as the present invention and which is incorporated by herein by reference. Second sensor $S_2$ thus measures a rate-control parameter related to changes in fluid pressure in the heart associated with its mechanical activity and contractility ($RCP_{press}$), and provides a second sensor output ($Output_{press}$) which is proportional to the magnitude of the change in fluid pressure in the patient's heart. In the preferred embodiment, second sensor output $S_2$ is processed to derive a peak positive time derivative of the fluid pressure applied to the pressure sensor $S_2$ within the right venricle of the patient's heart (i.e., $dP/dt_{max}$).

Pacemaker 100 is schematically shown electrically coupled via a pacing lead 102 to a patient's heart 104. Lead 102 includes an intracardiac electrode 106 and second sensor $S_2$ which are located near the distal end of lead 102 and positioned within the right ventricle (RV) of the patient's heart. Lead 102 can carry either unipolar or bipolar electrodes as is well known in the art. In the preferred embodiment, the lead 102 which couples pacemaker 100 to the ventricular endocardium can comprise a steroid-tipped, unipolar lead with an integral pressure transducer of the type described above. Electrode 106 is coupled via suitable lead conductor 102a through input filter capacitor 108 to node 110 and to the input terminals of an Input/Output Circuit shown at block 112. Output from first sensor $S_1$ is coupled to Input/Output Circuit 112. Output from second sensor $S_2$ is also coupled to Input/Output Circuit 112 via suitable lead conductor 102b.

Input/Output Circuit 112 contains the operating input and output analog circuits for digital controlling and timing circuits necessary for the detection of electrical signals derived from the heart, such as the cardiac electrogram, output from the first sensor output $S_1$, and output from the second sensor output $S_2$, as well as for the application of stimulating pulses to the heart to control its rate as a function thereof under the control of software-implemented algorithms in a Microcomputer Circuit shown at 114.

Microcomputer Circuit 114 comprises an On-Board Circuit 116 and an Off-Board Circuit 118. On-Board Circuit 116 includes a microprocessor 120, a system clock 122, and on-board RAM 124 and ROM 126. Off-Board Circuit 118 includes an off-board RAM/ROM Unit 128. Microcomputer Circuit 114 is coupled by Data Communication Bus 130 to a Digital Controller/Timer Circuit shown at 132. Microcomputer Circuit 114 may be fabricated of custom IC devices augmented by standard RAM/ROM components.

It will be understood by those skilled in the art that the electrical components represented in FIG. 1 are powered by an appropriate implantable-grade battery power source (not shown).

An antenna 134 is connected to Input/Output Circuit 112 for purposes of uplink/downlink telemetry through a radio frequency (RF) Transmitter/Receiver Circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier, as substantially described in U.S. Pat.

No. 5,127,404, issued on Jul. 7, 1992, entitled "Telemetry Format for Implantable Medical Device", which is held by the same assignee as the present invention and which is incorporated herein by reference. A reed switch 153 is connected to Input/Output Circuit 112 to enable patient follow-up via disabling the sense amplifier 146 and enabling telemetry and programming functions, as is known in the art.

A Crystal Oscillator Circuit 138, typically a 32,768 Hz crystal-controlled oscillator, provides main timing clock signals to Digital Controller/Timer Circuit 132. A Vref/Bias Circuit 140 generates a stable voltage reference and bias currents for the analog circuits of Input/Output Circuit 112. An ADC/Multiplexer Circuit (ADC/MUX) 142 digitizes analog signals and voltages to provide telemetry and replacement time-indicating or end-of-life function (EOL). A Power-on-Reset Circuit (POR) 144 functions to initialize the pacemaker 100 with programmed values during power-up, and reset the program values to default states upon the detection of a low battery condition or transiently in the presence of certain undesirable conditions such as unacceptably high EMI, for example.

The operating commands for controlling the timing of the pacemaker depicted in FIG. 1 are coupled by bus 130 to Digital Controller/Timer Circuit 132 wherein digital timers set the overall escape interval of the pacemaker, as well as various refractory, blanking and other timing windows for controlling the operation of the peripheral components within Input/Output Circuit 132.

Digital Controller/Timer Circuit 132 is coupled to a sense amplifier (SENSE) 146 and an electrogram (EGM) amplifier 148 for receiving amplified and processed signals picked up from electrode 106 through lead conductor 102a and capacitor 108 representative of the electrical activity of the patient's heart 104. SENSE amplifier 146 produces a sense event signal for re-setting the escape interval timer within Circuit 132. The electrogram signal developed by EGM amplifier 148 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention and which is incorporated by herein by reference. An output pulse generator 150 provides the pacing stimulus to the patient's heart 104 through an output capacitor 107 and lead 102 in response to a paced trigger signal developed by Digital Controller/Timer Circuit 132 each time the escape interval times out, or an externally transmitted pacing command has been received, or in response to other stored commands as is well known in the pacing art.

Digital Controller/Timer Circuit 132 is coupled to a processing/amplifying circuit (ACTIVITY) 152 for receiving amplified and processed sensor output (Output$_{act}$) from first sensor S$_1$ and associated ACTIVITY circuitry which is representative of activity. Digital Controller/Timer Circuit 132 is coupled to a processing/amplifying circuit (PRESSURE) 154 for receiving amplified and processed sensor output (Output$_{press}$) from second sensor S$_2$ through lead conductor 102b representative of changes in fluid pressure in the patient's heart 104, for use in rate response control, and others functions as desired.

In a preferred embodiment of the present invention, pacemaker 100 is capable of operating in various non-rate-responsive modes which include VVI, VOO and VVT, as well as corresponding rate-responsive modes of VVIR, VOOR and VVTR. Further, pacemaker 100 can be programmably configured to operate such that it varies its rate only in response to one selected sensor output, or in response to both sensor outputs, if desired (i.e., utilizing either or both of Output$_{act}$ or Output$_{press}$).

PART II. DEFINITIONS

For purposes of describing this invention, a definition of additional relevant terms follows:

Detection Window—A 170 mSec window beginning 30 mSec after a paced or sensed event used to detect the presence of a pressure signal indicative of cardiac contraction.

Loss-of-Capture (LOC)—Processing by pacemaker 100 detects the absence of a pressure signal in the detection window after a paced event. This lack of stimulated cardiac contraction is labeled Loss-of-Capture.

Lower Rate (LR)—A value supplied by the clinician which establishes a lower boundary on the pacing rate. If the sensors are disabled, or their sensor outputs are not large enough to increase rate, the lower rate is the stimulus rate. With rate response, the allowed programmable values for LR range from 40 pulses per minute (ppm) to 100 ppm at 1 ppm intervals.

Metric—The programmed (selected) output stimulus parameter (pulse width or pulse amplitude) selected to be modified in the response to Loss-of-Capture and during the Recovery sequence.

Non-Metric—The non-selected output stimulus parameter (pulse width or pulse amplitude). The non-metric parameter is changed only at the maximum output stimulus during response to Loss-of-Capture.

$P_{max}$—Processing by pacemaker 100 determines the maximum signal level in the pressure waveform from pressure circuit 154 during a detection window.

$P_{min}$—Processing by pacemaker 100 determines the minimum signal level in the pressure waveform from pressure circuit 154 during a detection window.

Pulse Pressure Average (PRESS.AVG)—Dynamic pressure sensor S$_2$ is disposed in the right ventricle (RV) of the patient's heart to sense fluid pressure therein (RCP$_{press}$), and to provide a sensor output (Output$_{press}$) related to changes in the fluid pressure associated with the heart's mechanical activity and contractility. Processing by pacemaker 100 of Output$_{press}$ yields a peak pulse pressure (PRESS.PK) which is proportional to the magnitude of such RV pressure changes. Each sensed or paced RV event will yield a peak pulse pressure signal. In the preferred embodiment, a running average of the last 16 valid PRESS.PK values are used to determine an average peak pulse pressure value, referred to as the "PRESS.AVG". Pacemaker 100 tests for validity of each peak pulse pressure value on a sample-by-sample basis, based upon the requirement that the sampled PRESS.PK value must be equal to or greater than, 4 mm Hg. Values below this validity threshold are ignored. Once determined, PRESS.AVG is used to detect capture on a cycle-to-cycle basis.

Recovery—Pacemaker 100 automatically attempts to adjust output stimulus parameters 1 hour after a Loss-of-Capture sequence. The metric parameter is adjusted in small increments toward it's programmed value.

Response to LOC—Pacemaker 100 automatically responds to a LOC by increasing the output pulse width and/or amplitude in a controlled response to enable rapid restoration of cardiac stimulation.

Threshold—A programmable threshold of continuously averaged peak pulse pressure value based upon a percentage of this stored peak value. The programmable range is 25–75% in 12.5% steps.

Upper Rate (UR)—A value supplied by the clinician which limits the maximum stimulation rate when the rate responsive modes for activity, pressure, or both combined, are in effect, or when response to loss-of-capture pacing is occurring such that the pacing rate generated by pacemaker 100 does not become hemodynamically excessive. The allowed programmable values range from 100 ppm to 175 ppm at 5 ppm intervals, provided UR must also be at least 20 ppm greater than Lower Rate (LR) and Resting Rate (REST.RATE).

PART III. SENSORS

A brief description of measurement of the rate control parameter for activity ($RCP_{act}$) now follows. The activity sensor $S_1$ sensor employed is a piezoelectric crystal transducer of the type described in the above-mentioned '378 Anderson et al. patent, which is mounted to the interior surface of the pacemaker can as disclosed therein. Sensor $S_1$ generates a sensor output ($Output_{act}$) due to deflection of the pacemaker can as a result of compression waves within the body caused by physical movement of the body. Processing by ACTIVITY circuit 152 is performed, such that each event in which the amplitude of $Output_{act}$ exceeds a programmed Activity Threshold (ACT. THRESH) is then counted and retained in an Activity Count (ACT.COUNT) of pacemaker 100. ACT.COUNT is used to calculate the activity-based Target Rate ($STR_{act}$) on a cycle-to-cycle basis.

A brief description of measurement of the rate control parameter for pressure ($RCP_{press}$) now follows. The pressure sensor $S_2$ sensor employed is a dynamic pressure sensor of the type described in the above-mentioned '813 Anderson et al. patent. Sensor $S_2$ is disposed in the right ventricle (RV) of the patient's heart to sense fluid pressure therein ($RCP_{press}$), and to provide a sensor output ($Output_{press}$) related to changes in the fluid pressure associated with the heart's mechanical activity and contractility. Processing by PRESSURE circuit 154 of $Output_{press}$ yields a peak positive first time derivative thereof ($dP/dt_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dP/dt_{max}$ value, referred to as the "Pressure (dP/dt) Average" or "dP/dt. AVG". Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value associated with the patient's Resting Rate (REST.PRESS). In the preferred embodiment, this validity range is defined as $dP/dt_{max}$ values between 25% to 400% of REST.PRESS. Values outside this validity range are ignored. Once determined, PRESS.AVG is used to calculate the pressure-based Sensor Target Rate ($STR_{press}$) on a cycle-to-cycle basis.

It will be understood, however, that the present invention can be practiced with more than two sensors, or with sensors of a type other than the ones above described. In the preferred embodiment, however, various advantages are obtained by the use of the particular sensors in the specific combination stated above.

For example, an activity-based sensor provides a fast and repeatable response to physical activity. Sensors of this type have been exhaustively reported in clinical literature, and their safety and efficacy are well-documented. Additionally, such sensors offer the advantage of being less affected by changes in a patient's health or disease status, and thus provide more predictable behavior over time. However, there are also theoretical and practical limitations to the behavior of activity sensors. For example, they respond only to physical activity. Therefore, patients undergoing other types of physiological stresses which would normally evoke a heart rate response, such as thermal stress associated with normal exposure to wide variations in ambient temperature, or postural stress associated with changing from lying down to an erect position, will tend to obtain only very limited rate adjustment and their adjustment to such stresses will thus be less than entirely adequate. Additionally, the time course of rate recovery after an activity event tends to be limited by the design constraints of the pacemaker system which are not generally capable of providing a highly physiologically-based recovery function.

Consequently, the preferred embodiment also incorporates a dynamic pressure sensor for continuous measurement of cardiac pressures on a beat-by-beat basis. This sensor provides for more physiological responses than activity alone, and helps to complement the rate response provided by the activity sensor. The sensed physiologic variable in this system comprises the rate of increase in pressure within the right ventricle of the heart (i.e., a peak positive dP/dt). This variable is related to the vigor of contraction of the cardiac muscle, which in turn is regulated by the autonomic nervous system. Thus, any stress which elicits a response by the autonomic nervous system in the patient (and would cause a heart rate response in a normal individual), will also yield a heart rate response in the patient by means of the pacemaker system of the present invention. Additionally, the time course of recovery of the cardiac pressure following stresses follows the physiologic time course determined by the status of the autonomic nervous system, such that the present device will provide for pacing rate recovery which is more physiological than that which can be provided by activity sensors alone.

It can thus be appreciated that the particular sensor combination described above yields significantly improved rate response function for pacemaker 100.

PART IV. AUTOMATIC CAPTURE AND THRESHOLD-SEEKING FEATURES

Specific details of the auto-capture and threshold-seeking features of the present invention follow below. Of related interest are U.S. patent application Ser. No. 07/958,194, filed Oct. 7, 1992, for AUTOMATIC CARDIAC CAPTURE RESTORATION AND THRESHOLD-SEEKING METHOD AND APPARATUS, and U.S. patent application Ser. No. 08/122,258, filed Sep. 15, 1993, for PACEMAKER WHICH ADAPTS TO MINIMIZE CURRENT DRAIN AND PROVIDE DESIRED CAPTURE SAFETY MARGIN, which applications are also assigned to the assignee of the present application, and which applications are also expressly incorporated by reference. Those applications provide additional details about auto-capture and threshold-seeking functions which may be modified to operate in conjunction with the present invention.

Capture Verification

Physiological changes in the patient may alter the thresholds from the initial programmed value or values, and can lead to loss of capture, with inadequate amplitude or pulse width. The pacemaker 100 is capable of detecting loss of capture via a capture detector using the pressure sensor $S_2$ and evoked responses, for example, as is known in the art. Thus, a "CAPTURE DETECT" message is produced when capture is present, and a "NO CAPTURE DETECT" message is produced during a loss-of-capture episode.

Figure 2:
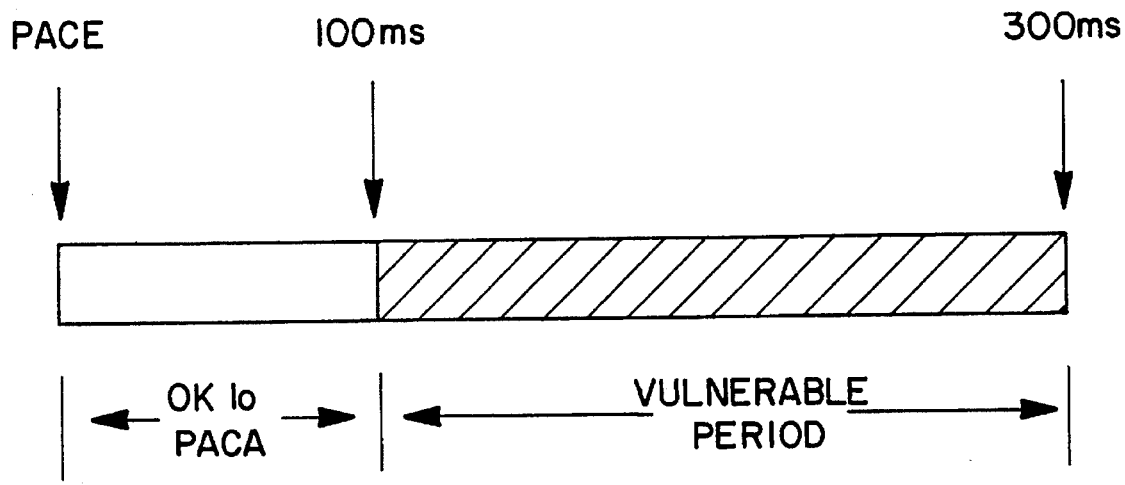
FIG. 2 is a simple pacing timing diagram showing the Vulnerable Period.

Either a CAPTURE DETECT message or a NO CAPTURE DETECT message occurs in a predefined capture detect window (CDW) following a pacing pulse during capture verification. The duration of the CDW may be programmed to a suitable value. A full-amplitude backup pulse is rapidly delivered for safety purposes. The backup pulse occurs within 100 ms in the preferred embodiment, which is before the Vulnerable Period begins. FIG. 2 is a timing diagram illustrating the Vulnerable Period and a safe backup pacing interval. Note that in prior art pacemakers, the backup pulse would not be delivered until at least 300 ms after the primary pacing pulse.

The backup pacing pulse restarts the pacemaker escape interval. The pacemaker 100 then methodically changes the regular pacing pulses as described below, until capture is achieved by the regular pacing pulses.

After each loss-of-capture episode, the pulse width of the regular pacing pulse is increased by 0.1 ms ("Maximum Pulse Width ") in the preferred embodiment until either capture is regained or the pulse width reaches 1.0 ms, whichever occurs first. If the Maximum Pulse Width is reached and capture has still not occurred (following the regular pacing pulse) the pulse amplitude is incremented in predefined amplitude steps ("Amp Step") until capture is regained.

In order to periodically determine more efficient pacing pulse parameters (i.e., parameters that result efficient battery drain characteristics) the pulse width and amplitudes can be decreased to programmed Minimum Pulse Width and Minimum Amplitude values. If loss of capture occurs, the pacing pulse parameters are adjusted in a stepwise fashion as described above. Also programmable for use as described infra., are a "Maximum Pulse Width" value and a "Maximum Amplitude" value.

The interval between each regular pacing pulse and each CAPTURE DETECT signal is measured and stored in memory for later use. A "Stimulus to Detect Maximum" value and a "Stimulus to Detect Minimum" value are stored, representing the maximum amount of delay observed between a pacing pulse and a CAPTURE DETECT signal, and the minimum amount of delay observed between a pacing pulse and a CAPTURE DETECT signal, respectively. When the CAPTURE DETECT interval exceeds the Stimulus to Detect Maximum, the value of the Stimulus to Detect Maximum is increased by an amount equal to one clock cycle. Likewise, when the CAPTURE DETECT interval is less than the Stimulus to Detect Minimum, the value of the Stimulus to Detect Minimum is decreased by an amount equal to one clock cycle.

At the beginning of the capture verification program, the Stimulus to Detect Maximum and the Stimulus to Detect Minimum are both initialized to the first observed value of the capture detect interval. Subsequently, these values are periodically updated as described supra. For example, the thresholds may be re-determined once a day.

More efficient pacing threshold parameters are established by either of the threshold-seeking approaches described below. During the operation of the threshold-seeking algorithms, the pacing rate is elevated to minimize the effects of rate drops cause by loss of capture.

Threshold-Seeking—First Approach

The pacing pulse can be rapidly optimized (coarse adjustment) using the following algorithm.

To insure safety during the threshold seeking process a pair of pacing pulses is delivered during each cardiac cycle. The first pulse is the regular (or primary) pacing pulse which the pacemaker is seeking to optimize for longer battery life. The second is the backup safety pulse delivered within 100 ms after the first pulse at full amplitude and 0.75 ms pulse width in the preferred embodiment, to insure that the heart is always captured when the first pulse fails to effect a capture.

The time from the delivery of the first pacing pulse to a CAPTURE DETECT signal is measured and compared to the stored Stimulus to Detect Minimum and Stimulus to Detect Maximum values. If the CAPTURE DETECT signal time falls between the Stimulus to Detect Minimum and the Stimulus to Detect Maximum values, the first pacing pulse is assumed to have captured the heart. The threshold seeking algorithm first sets the amplitude of the first pulse to its maximum value and a predetermined pulse width—0.5 ms for example.

The amplitude of the first pacing pulse is decremented in successive cardiac cycles according to the following equation:

$$P = \frac{(CY - CN)}{2} + CN \quad (1)$$

where P is the amplitude of the first pacing pulse in the next cardiac cycle, CY is the smallest amplitude of all previous cycles which captured the heart, and CN is the largest amplitude of the previous cycles which did not capture the heart. CY and CN are initialized to the Maximum amplitude and Minimum amplitude values, respectively, and are updated with each successive threshold seeking cycle.

The threshold seeking sequence is complete in the preferred embodiment when the quantity CY-CN is less than n times a programmable Amplitude Resolution. In the preferred embodiment, n equals two, and the Amplitude Resolution is set equal to 0.2 volts.

After the threshold amplitude is determined, Equation (1) is then used to determine the threshold pulse width. During the pulse width search P is the pulse width of the first pacing pulse in the next cardiac cycle, CY is the smallest pulse width of all previous cycles which captured the heart, and CN is the largest pulse width of the previous cycles which did not capture the heart. CY and CN are initialized to the Maximum pulse width and Minimum pulse width values, respectively, and are updated with each successive threshold seeking cycle.

The threshold seeking sequence is complete in the preferred embodiment when the quantity CY-CN is less than n times a programmable Pulse Width Resolution. In the preferred embodiment, n equals two, and the Amplitude Resolution is set equal to 0.1 volts.

During the pulse width search the amplitude is set to twice the optimized value (determined during the amplitude search). When the pulse width search is complete, the amplitude is reset to its optimized value.

Figure 3:
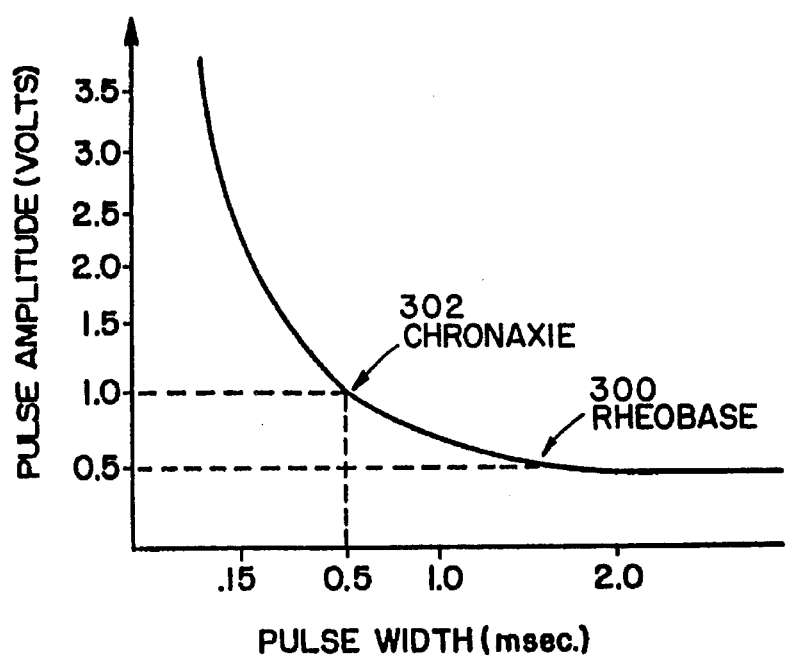
FIG. 3 is a typical strength-duration curve for cardiac stimulation signals.

Both the amplitude and pulse width thresholds are stored to provide rheobase 300 and chronaxie 302 points for an approximate strength-duration curve, much like the example in FIG. 3 (shown only for illustrative purposes). The strength-duration curve may be used for various diagnostic purposes.

Threshold-Seeking—Second Approach

The pacing pulse can be optimized with finer tuning in a more gradual way by following the algorithm described below.

First, the amplitude is set to the programmed Maximum Amplitude (e.g., 5 volts), and the pulse width is set to a predetermined value such as 0.5 ms. Pacing pulse pairs are delivered as described supra., with the first pulse being the desired pacing pulse, and the second pulse being a safety pulse at full amplitude so that capture is maintained when the first pulse fails to capture. The amplitude is reduced in programmable coarse steps ("Coarse Amp Step") at first until the first pulse fails to capture the heart, or until the programmed Minimum Amplitude is reached-whichever occurs first. Coarse Amp Step is set equal to 0.5 volts in the preferred embodiment, but may be any other feasible value.

Following loss of capture (by the first pulse) the amplitude is incremented by Coarse Amp Steps until the first pulse again captures the heart. Then, the amplitude is decremented by programmable fine amplitude steps ("Fine Amp Step") until capture is lost (by the first pulse). The amplitude where capture is lost is deemed the threshold amplitude. Fine Amp Step is set equal to 0.1 volts in the preferred embodiment, but may be any other feasible value.

If desired, a safety margin (such as 0.2 volts, for example) may be added to the amplitude.

Following the amplitude search, the algorithm performs a pulse width search in much the same manner. The amplitude is set equal to twice the value determined in the amplitude search. The pulse width is first set equal to the programmed Maximum Pulse Width (1.0 ms in the preferred embodiment). The pulse width is reduced in programmable coarse steps ("Coarse PW Step") at first until the first pulse fails to capture the heart, or until the programmed Minimum Pulse Width is reached—whichever occurs first. Coarse PW Step is set equal to 0.1 ms in the preferred embodiment, but may be any other feasible value.

Following loss of capture (by the first pulse) the pulse width is incremented by Coarse PW Steps until the first pulse again captures the heart. Then, the pulse width is decremented by programmable fine pulse width steps ("Fine PW Step") until capture is lost (by the first pulse). The pulse width where capture is lost is deemed the threshold pulse width.

When the pulse width threshold is determined, both the amplitude and pulse width are set equal to their determined threshold values.

The amplitude and pulse width searches can occur over a longer period of time by delaying each adjustment (i.e., Coarse Amp Step, Fine Amp Step, Coarse PW Step and Fine PW Step) by a programmed time interval or number of cardiac cycles.

A strength-duration curve is approximated using the method described supra.

Variations and modifications to the present invention are possible given the above disclosure. However, such variations and modifications are intended to be within the scope of the invention claimed by this letters patent. For example, the present invention is limited to use with single chamber pacemakers, and will also function with dual chamber pacemakers and the various dual chamber pacing modes.

We claim:

1. A pacemaker capable of automatically seeking stimulation thresholds comprising:

a pulse delivery and generator means for being coupled to a patient's heart to deliver primary and backup stimulation pulses;

a means coupled to receive indications of the capture of said patient's heart in response to a stimulation pulse and in response to said detection generating a signal value related to the amount of time between the delivery of said primary stimulation pulse and said detected capture if one is detected, means for determining amplitude and pulse width thresholds of primary pacing pulses based on said time related signal value;

and wherein said backup stimulating pulses are delivered after said primary pulses.

2. A pacemaker as set forth in claim 1 wherein said backup pulse is delivered via said pulse delivery and generator means to said patient's heart prior to the start of a predefined Vulnerable Period of approximately 100 ms from the delivery of the primary pulse and wherein said backup pulse has a combination of amplitude and pulse width characteristics sufficient to effect capture as determined by said means coupled to receive indications of the capture of said patient's heart.

3. A pacemaker as set forth in claim 1 wherein said pacemaker further comprises:

(a) memory means for holding the value of a variable in association with each heart cycle in which a primary pacing pulse captures the heart as determined by said means coupled to receive indications of the capture of said patient's heart, (b) processor means for calculating a primary stimulation pulse characteristic according to the equation:

$$P = \frac{(CY - CN)}{2} + CN,$$

wherein P is said primary stimulation pulse characteristic which equals a pulse energy variable defined either by one of "amplitude" at a given pulse width, and by "pulse width" at a given amplitude, CY is the smallest one of such pulse energy variables in previous cycles of the patient's heart in which said heart was captured by a primary stimulation pulse and CN is the largest pulse energy variable of such pulse energy variables that was not captured by a primary stimulation pulse, (c) program means for iteratively causing said processor means to execute said calculations during threshold seeking.

4. An automatic stimulation signal threshold seeking method for automatically seeking stimulation thresholds for adjusting primary pulses which will be used during pacing in a pacemaker for stimulating by delivering pulses of energy to a patient's heart, said method comprising the steps of:

delivering both a primary and a backup stimulation pulse at each cardiac cycle during the operation of threshold seeking;

detecting the capture of a patient's heart in response to a primary stimulation pulse; and determining amplitude and pulse width thresholds of primary pacing pulses.

5. A method as set forth in claim 4 wherein said delivering step delivers said backup stimulation pulse is before the Vulnerable Period, approximately 100 ms after delivering said primary pulse.

\* \* \* \* \*